US012601673B2

(12) United States Patent
Miloud et al.

(10) Patent No.: US 12,601,673 B2
(45) Date of Patent: Apr. 14, 2026

(54) FIXABLE VIABILITY DYES AND THEIR USES

(71) Applicant: Beckman Coulter, Inc., Brea, CA (US)

(72) Inventors: Tewfik Miloud, Marseilles (FR); Shankar Pattabhiraman, Chennai (IN); James Tung, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 904 days.

(21) Appl. No.: 17/256,523

(22) PCT Filed: Jul. 12, 2019

(86) PCT No.: PCT/US2019/041651
§ 371 (c)(1),
(2) Date: Dec. 28, 2020

(87) PCT Pub. No.: WO2020/014639
PCT Pub. Date: Jan. 16, 2020

(65) Prior Publication Data
US 2021/0278331 A1 Sep. 9, 2021

(30) Foreign Application Priority Data
Jul. 12, 2018 (IN) ............................ 201811026074

(51) Int. Cl.
*G01N 15/14* (2024.01)
*G01N 15/149* (2024.01)
*G01N 33/50* (2006.01)
*G01N 33/58* (2006.01)

(52) U.S. Cl.
CPC ......... *G01N 15/14* (2013.01); *G01N 33/5094* (2013.01); *G01N 33/582* (2013.01); *G01N 15/149* (2024.01)

(58) Field of Classification Search
None
See application file for complete search history.

(56) References Cited

U.S. PATENT DOCUMENTS

| | | | |
|---|---|---|---|
| 2006/0188445 | A1 | 8/2006 | Ou et al. |
| 2008/0241820 | A1 | 10/2008 | Krutzik et al. |
| 2011/0038798 | A1 | 2/2011 | Brindle et al. |
| 2011/0065094 | A1 | 3/2011 | Kimura et al. |
| 2011/0312012 | A1 | 12/2011 | Skinderso et al. |
| 2011/0312013 | A1 | 12/2011 | Skindersoe et al. |
| 2016/0131658 | A1 | 5/2016 | Skinderso et al. |

FOREIGN PATENT DOCUMENTS

| | | | |
|---|---|---|---|
| CN | 104011542 | 8/2014 | |
| CN | 112352160 | 2/2021 | |
| EP | 0 231 2943 | 4/2011 | |
| IN | 202047053207 | 1/2021 | |
| KR | 10-2014-0100536 | 8/2014 | |
| KR | 10-2015-0102075 | 9/2015 | |
| KR | 1020210018332 | 2/2021 | |
| WO | 2007/097377 | 8/2007 | |
| WO | 2010/006616 | 1/2010 | |
| WO | WO-2010006615 A2 | 1/2010 | |
| WO | 2017/161182 | 9/2017 | |
| WO | WO-2017197144 A1 * | 11/2017 | ............. C09K 11/06 |
| WO | WO-2020014639 A1 | 1/2020 | |

OTHER PUBLICATIONS

Subrahmanyam, P.B. et al. 2018. Distinct predictive biomarker candidates for response to anti-CTLA-4 and anti-PD-1 immunotherapy in melanoma patients. Journal for ImmunoTherapy of Cancer 6(18): 1-14; specif. pp. 3, 6 (Year: 2018).*

Samson, A.L. et al. 2012. Nucleocytoplasmic coagulation: an injury-induced aggregation event that disulfide crosslinks proteins and facilitates their removal by plasmin. Cell Reports 2: 889-901; specif. pp. 889, 890, 891, 893, 900 (Year: 2012).*

Perfetto, S.P. et al. 2010. Amine-reactive dyes for dead cell discrimination in fixed samples. Current Protocols in Cytometry, pp. 9.34.1-9.34.14; specif. p. 9.34.1, 9.34.3 (Year: 2010).*

Yi, M.C. et al. 2016. Thiol-disulfide exchange reactions in the mammalian extracellular environment. Annual Review of Chemical and Biomolecular Engineering 7: 197-222; specif. pg. 199 (Year: 2016).*

Comini, M.A. 2016. Rev. Measurement and meaning of cellular thiol:disulfide redox status. Free Radical Research 50(2): 246-271; specif. pp. 246, 251, 255 (Year: 2016).*

PubChem DOTA maleimide. Maleimide-DOTA. Retrieved on Feb. 5, 2024. Downloaded from the internet: <https://pubchem.ncbi.nlm.nih.gov/compound/Maleimide-DOTA> pp. 1-2 (Year: 2024).*

PubChem Alexa fluor maleimide. Alexa Fluor 488 C5 maleimide. Retrieved on Feb. 5, 2024. Downloaded from the internet: <https://pubchem.ncbi.nlm.nih.gov/substance/332833356> pp. 1-3 (Year: 2024).*

Fluorophore Table. abcam. Datasheet [online]. Downloaded on: Nov. 6, 2024; Retrieved from: <https://www.abcam.com/ps/pdf/protocols/fluorophore%20table.pdf> p. 1 (Year: 2024).*

"Indian Application Serial No. 202047053207, First Examination Report mailed Aug. 16, 2021", with English translation, 6 pages.

"Japanese Application Serial No. 2020-573462, Notification of Reasons for Refusal mailed Jan. 7, 2022", with English translation, 8 pages.

"Korean Application Serial No. 10-2020-7037737, Notice of Preliminary Rejection mailed Jan. 27, 2022", with English translation, 9 pages.

"European Application Serial No. 19749885.0, Response Filed Sep. 1, 2021 to Communication under Rules 161(1) and 162 EPC mailed Feb. 19, 2021", 10 pgs.

(Continued)

*Primary Examiner* — Michelle F. Paguio Frising
*Assistant Examiner* — Sharon M. Papciak
(74) *Attorney, Agent, or Firm* — Merchant & Gould P.C.

(57) ABSTRACT

The present invention provides compositions and methods useful for detecting live cells and dead cells in a cell sample. The methods rely on labelling compounds comprising a maleimide moiety linked to a label.

10 Claims, 4 Drawing Sheets

(56) References Cited

OTHER PUBLICATIONS

Subrahmanyam, Priyanka B, "CyTOF Measurement of Immunocompetence across Major Immune Cell Types", Current Protocols in Cytometry vol. 82, 9.54.1-9.54.12, (Feb. 13, 2018).
"Australian Application Serial No. 2019300055, First Examination Report mailed Mar. 1, 2022", 4 pages.
"International Application Serial No. PCT/US2019/041651, International Search Report mailed Oct. 23, 2019", 5 pgs.
"International Application Serial No. PCT/US2019/041651, Written Opinion mailed Oct. 23, 2019", 7 pgs.
Subrahmanyam, P, et al., "Distinct Predictive Biomarker Candidates for Response to Anti-CTLA-4 and anti-PD-1 Immunotherapy in Melanoma Patients", Journal for ImmunoTherapy of Cancer, 6(18), (Mar. 6, 2018), 14 pgs.
Akinloye, Oluyemi et al., "Peptide-based fluorescence biosensors for detection/measurement of nanoparticles", Anal Bioanal Chem, 409, 4, Feb. 28, 2017.
Australian Application Serial No. 2019300055, Notice of Acceptance of Patent Application mailed Jul. 13, 2022, 3 pages.
Chinese Notice of Intention to Grant and Search Report in Application 201980044222.4, mailed Jul. 2, 2024, 10 pages.
Dolci, Elena et al., "Maleimides as a Building Block for the Synthesis of High Performance Polymers", (2016) Polymer Reviews 56; 512-556.
Dupas, Nathalie et al., "ViaKrome Fixable Viability Dyes: A New Approach to Dead Cell Discrimination for Intracellular Multicolor Flow Cytometry Application", the Journal of Immunology, vol. 204, No. Suppl 1, May 1, 2020, 86.56, abstract, XP093050091.
European Application 19749885.0, Communication pursuant to Article 94(3) EPC mailed Jun. 2, 2023, 6 pages.
European Summons to attend oral proceedings in U.S. Appl. No. 19/749,885, mailed Apr. 12, 2024, 6 pages.
Japanese Application 2020-573462, Decision to Grant a Patent mailed May 2, 2022, English translation, 2 pages.
Korean application 10-2020-7037737, Notice of Rejection mailed Sep. 8, 2022, 2 pages.
Korean application 10-2020-7037737, Written Decision on Registration, mailed Mar. 28, 2023, 3 pages.
Li, Feng et al., "Fluorescence imaging of APP in Alzheimer's disease with quantum dot or Cy3: a comparative study", Journal of Central South University (Medical Sciences), Issue 9, Sep. 15, 2010. pp. 903-909.
PCT International Preliminary Report on Patentability in Application PCT/US2019/041651, mailed Jan. 16, 2020, 9 pages.
Singapore 1st Written Opinion in Application 11202011500U, mailed Feb. 28, 2022, 5 pages.
Singapore 2nd Written Opinion in Application 11202011500U, mailed Jun. 26, 2023, 6 pages.
Song et al., "Practical synthesis of maleimides and coumarin-linked probes for protein and antibody labelling via reduction of native disulfides", (2009), Organic Biomol Chem 7(17):3400-3406.

* cited by examiner

FIXABLE VIABILITY DYES AND THEIR USES

RELATED APPLICATION

This application is a U.S. National Stage Filing under 35 U.S.C. 371 from International Application No. PCT/US2019/041651, filed on Jul. 12, 2019, and published as WO 2020/014639 on Jan. 16, 2020, which application claims priority of Indian Patent Application number 201811026074, filed on Jul. 12, 2018. The entire content of said application is herein incorporated for all purposes.

FIELD OF THE INVENTION

This invention relates to compositions and methods useful in distinguishing live cells from dead cells in a cell sample. The compositions and methods are suitable for use with methods of staining intracellular targets as well as extracellular targets in cells from the cell sample.

BACKGROUND OF THE INVENTION

When performing a flow cytometry staining, DNA binding dyes are often used to differentiate between live and dead cells. DNA binding dyes, such as 7-AAD and propidium iodide, do not stain live cells, but are able to reach and non-covalently bind the DNA of dead cells because their cell and nucleus membranes are permeabilized. However, DNA binding dyes cannot be used when intracellular staining is desired because, after fixation and permeablization used for intracellular staining procedures, the dyes will detach from the dead cells and stain the live cells.

One approach that has been developed to allow for intracellular staining in combination with detecting cell viability, is to stain cells prior to intracellular staining using N-hydroxysuccinimide (NHS)-ester dyes to differentiate between live and dead cells. NHS-ester dyes convalently bind to free NH2 groups. Live cells are stained at a “low intensity” because the NHS-Ester dye will stain only proteins expressed at the cell surface, while dead cells stain at a “high intensity” because the cells are permeabilized and the dyes are able to bind both intracellular and cell surface proteins. The NHS-ester dyes, however, are not water soluble and relatively unstable. As a result, the dyes must be aliquoted into volumes suitable for individual assays, kept at −20° C. as a lyophilized composition, and re-suspended in DMSO just prior to use.

There is a continuing need to develop new and improved rapid, high throughput cell viability assays, such as those using flow cytometry. The identification of reagent compositions useful in these applications is of particular importance. The present invention addresses these and other needs.

BRIEF SUMMARY OF THE INVENTION

The present invention provides methods for distinguishing dead cells from live cells in a cell sample. The methods comprise contacting the cell sample with a labelling compound of Formula I:

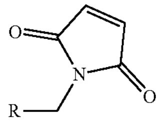

wherein R is a label, or a label attached through a linker, under conditions whereby the labelling compound binds free thiol groups on cell surface proteins on dead cells and live cells and preferentially crosses cell membranes of dead cells and binds free thiol groups on intracellular proteins in the dead cells; and detecting the label in the cell sample, thereby distinguishing dead cells from live cells in the cell sample by detecting increased labelling of the dead cells, as compared to live cells.

The method may further comprise labelling intracellular targets in the cells after the step of contacting the cell sample with the labelling compound. The labelling of intracellular targets can include fixing and permeabilizing the cells. In some embodiments, the method further comprises labelling extra cellular targets.

A number of labels can be used in the methods of the invention. The label may be a direct label, such as a fluorescent label.

In some embodiments, the methods are carried under conditions that include a pH of between about 6.5 and about 7.5.

The methods of the invention can result in labeling of dead cells that is at least about 20 times the labeling of live cells, often at least 500 time the labeling of live cells.

In some embodiments, the step of contacting includes incubating the cell sample with the labelling compound for between about 10 and about 60 minutes. The step of detecting the label in the cell sample can be carried out using a flow cytometer.

The cell sample can be any of a number of types. In some embodiments, the cell sample is a blood cell sample, for example, from a human.

The invention also provides kits for distinguishing dead cells from live cells in a cell sample. The kits comprise a container comprising a labelling compound of Formula I:

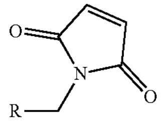

wherein R is a label, or a label attached through a linker, one or more containers comprising reagents for fixing and permeabilizing cells in the sample, and instructions on how to distinguish dead cells from live cells in a cell sample using the labelling compound.

The label may be a direct label, for example a fluorescent label.

In some embodiments, the labelling compound is provided in dry form. The kit may be suitable for distinguishing dead cells from live cells in a cell sample using a flow cytometer. The kit may further comprise labelled binding agents for detecting intracellular and/or extra cellular targets in the cell sample.

BRIEF DESCRIPTION OF THE DRAWINGS

FIG. 1 shows the results of the same samples that were stained with NHS-ester labeled with Violet Stain, Red Stain, or Far Red Stain.

FIG. 3A shows the results of PBMCs stained with ViaKrome 405 ("VK405") alone (I) or with a multicolor staining (II). FIG. 3B shows that the phenotyping of the population such as CD45+Lymphocytes [FIG. 3B(I), CD45+ cells], T cells expressing Granzyme B [FIG. 3B(II), CD3+GB+ cells], B cells expressing CD79a [FIG. 3B(III), CD19+CD79a+ cells)] and Monocytes [FIG. 3B(IV), CD14+ cells] is similar in presence or in absence of VK405.

DETAILED DESCRIPTION

Figure 1:
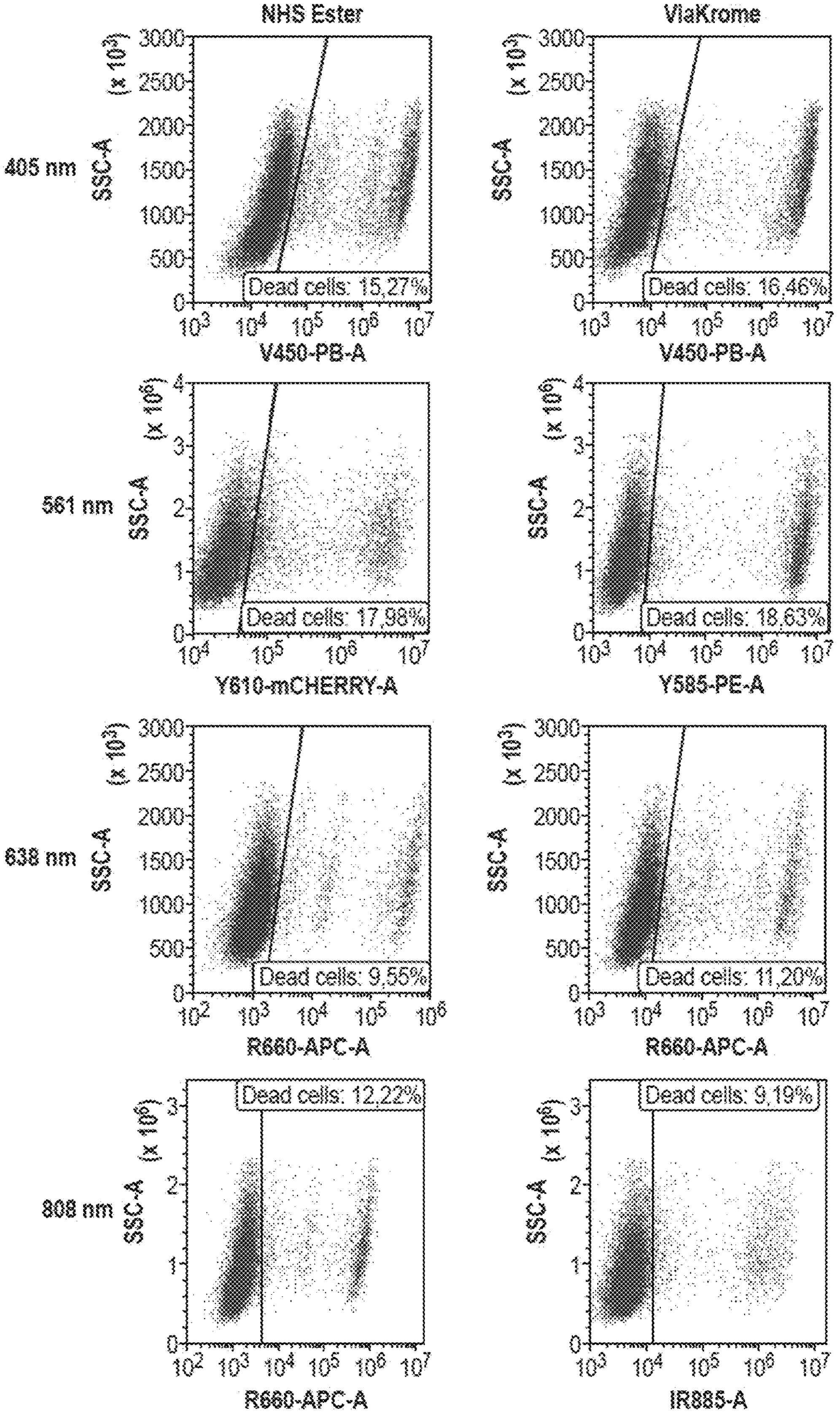
FIG. 1 shows histograms demonstrating greater fluorescence of dead Jurkat cells, as compared to live Jurkat cells as detected by flow cytometry using labelling compounds of the invention, i.e., ViaKrome 405, ViaKrome 561, ViaKrome 638, or ViaKrome 808.

The present invention provides methods useful for distinguishing live cells from dead cells in a cell sample. The methods rely on labelling compounds comprising a maleimide moiety linked to a label.

Labelling Compounds

The labelling compounds of the invention comprise a maleimide moiety linked to a label and have the general formula of Formula I:

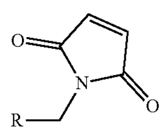

Where R is a label, or a label attached to a linker.

In some embodiments, the labeling compounds do not passively diffuse through cell membrane of live cells, i.e., they do not cross cell membrane of live cells unless the membranes are permeabilized. In some embodiments, the R does not comprise a 9-aminoacridine of Formula II:

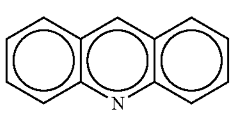

The reaction of maleimides with thiols is useful for bioconjugation and labeling of biomolecules such as proteins and peptides. Maleimides are electrophilic compounds which show high selectivity towards free thiols. Free thiols are present in proteins on cysteine residues. Cysteine residues commonly form cystine bridges, which stabilize protein tertiary structures. These disulfides do not react with maleimides. Thus, it is sometimes necessary to reduce disulfides prior to the conjugation to exclude oxygen from the reaction.

The labelling compounds of the invention remain bound to cellular proteins, even after treatment of the sample with a fixative. Thus, they are suitable for use in assays in which the cells are fixed for further analysis (e.g., labelling of intracellular targets, as described below). The labelling compounds are sometimes referred to as fixable labelling compounds or fixable viability dyes.

A label is a molecule or moiety that can be directly or indirectly detected. A directly detectable label is directly visualized and/or measured or otherwise identified so that its presence or absence can be detected. An indirectly detectable label is not itself detectable, but requires the attachment of a detectable secondary label after the labelling compound has reacted with free thiols in the target protein. Examples of labels include fluorescent molecules, enzymes (e.g., horseradish peroxidase), particles (e.g., magnetic particles), metal tags, chromophores, phosphors, chemiluminescers, specific binding molecules, useful as indirectly detectable labels (e.g., biotin and streptavidin, digoxin and anti-digoxin), and the like.

In a typical embodiment, the label is a fluorescent label, which is any molecule that can be detected via its inherent fluorescent properties. Suitable fluorescent labels include, but are not limited to, phycoerythrin (PE), phycoerythrin Cyanin 7 (PC7), phycoerythrin Texas red (ECD®), fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 Oregon green, green fluorescent protein (GFP), blue fluorescent protein (BFP), enhanced yellow fluorescent protein (EYFP), and luciferase. Additional labels for use in the present invention include: Alexa-Fluor dyes (such as: APC-Alexa Fluor 750 (AA750), Alexa Fluor 350, Alexa Fluor 430, Alexa Fluor 488, Alexa Fluor 546, Alexa Fluor 568, Alexa Fluor 594, Alexa Fluor 633, Alexa Fluor 660, and Alexa Fluor 680), conjugated polymer-based dyes, dendrimer-based dyes, quantum dots, and polymer dots.

The label can be attached to the maleimide moiety directly or through a linker. Suitable linkers are well known to those of skill in the art and will depend, for example, on the particular label. Examples of suitable linkers include SMCC, sulfo SMCC, and the like.

The labeling compounds thus have relatively large molecular weight, which renders them unable to cross the cell membrane without permeabilization, therefore they predominately stain dead cells instead of live cells. The positive read-out (staining of dead cells) is more efficient and accurate to quantify dead cells. Hence, in a multiparameter technology, such as flow cytometry, low staining of live cells leads to less compensation of data set, which facilitate the analysis and increases the accuracy of measurement of the other parameters.

The labelling compounds can be prepared according to methods known in the art (see, e.g., Dolci et al. (2016) Polymer Reviews 56:512-556 and Song et al. (2009) Org Biomol Chem 7:3400-3406), which are incorporated herein by reference. Alternatively, they may be purchased from commercial vendors, such as, for example, PromoKine and AAT Bioquest.

In some embodiments, the labelling compounds of the invention can be made by conjugating a maleimide to a label through a SMCC linker according to the synthetic scheme as follows:

Succinimidyl4 (N-maleimidomethyl) cyclohexane-1-carboxylate

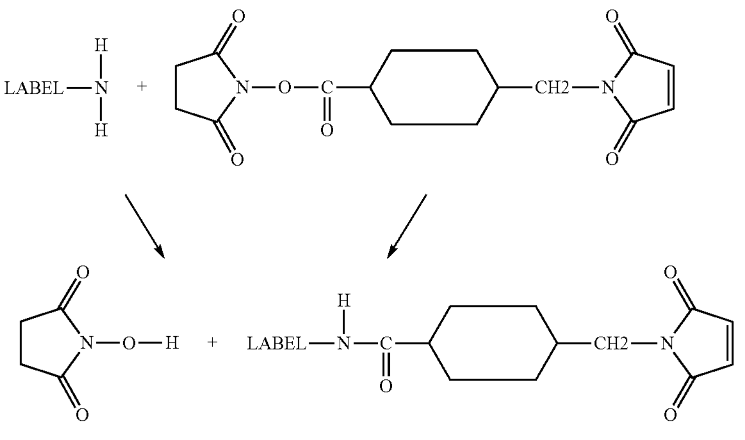

In some embodiments, the labeling compounds of the invention have a molecular weight that is greater than 300 g/mol, for example greater than 400 g/mol, greater than 500 g/mol, or greater than 600 g/mol. In some embodiments, the labeling compounds have a molecular weight that ranges from 300 g/mol to 3000 g/mol, e.g., from 600 g/mol to 2000 g/mol, or from 700 g/mol to 1800 g/mol.

In some case In some embodiments, the labeling compound used in the invention is one of ViaKrome 405, ViaKrome 561, ViaKrome 638, and ViaKrome 808. Each of these labeling compounds comprises a maleimide attached to a label as described above and the molecular weight of which are as follows.

Fluorochrome MW (g/mol)
ViaKrome 405 714.69
ViaKrome 561 836.78
ViaKrome 638 1186.27
ViaKrome 808 1647.66

The excitation and emission wavelength of the compounds are as follows:

Excitation/Emission
Fluorochrome (nm)
ViaKrome 405 402/425
ViaKrome 561 556/569
ViaKrome 638 638/652
ViaKrome 808 852/877

Assays to Detect Live and Dead Cells

The labelling compounds of the invention are conveniently used to distinguish live from dead cells in a cell sample. In the assay of the invention, cell surface proteins on both live and dead cells are stained by the labelling compounds. In dead cells, intracellular proteins are also stained because the cell membrane is permeabilized, giving the labelling compounds increased access to intracellular targets of dead cells. As a result, dead cells have increased labelling and signal intensity, as compared to live cells. The intensity of the signal from dead cells is typically at least about 10 times greater than that from live cells, usually about 50 times greater, and often about 250 greater and most often 1500 times greater.

The reaction between the labelling compounds of the invention and free thiols is most efficient at a neutral pH. In the typical embodiment, the labelling compounds are contacted with a cell sample at a pH between about 6.0 and about 8.0, usually between about 6.5 and about 7.5 and often about 7.2.

In a typical assay, cells from a cell sample are spun down and re-suspended in an appropriate buffer solution (e.g., PBS) to a desired cell density, for example, between about $0.5\times10^{6}$ and about $10\times10^{6}$ cells/ml, often between about $1\times10^{6}$ and about $2\times10^{6}$ cells/ml. The staining volume can be adjusted from about 50 to about 1000 μl. The solution comprising the cells is then contacted with the labelling compound of the invention. The labelling compound may be provided in dry form (e.g., as a dry spot in a reaction vessel) or can be added in a solution, which may comprise additional components, such as buffers, salts, and the like. If the labelling compound is provided in dry form, it is typically lyophilized The final concentration of the labelling compound in the cell sample is selected to ensure sufficient labelling of the cells in the sample. In a typical embodiment, the final concentration of the labelling compound will be between about 0.15 μg/ml and about 10 μg/ml, usually between about 1 μg/ml and about 5 μg/ml. The sample is then incubated with the labelling compound for a time to ensure sufficient labelling. The incubation time will typically be between about 10 and about 60 minutes, usually between about 20 and about 30 minutes. Those of skill can readily determine the appropriate solutions to use, the amount of labelling compounds and incubation times necessary to achieve sufficient labeling, which will depend, for example, on the nature of the cell sample, the detectable label, and the like.

The cell sample may be any sample comprising cells whose viability is to be tested. Samples can include eukaryotic cell cultures (e.g., animal, plant, yeast, or fungal cells), or prokaryotic cell cultures (e.g., bacterial cells). The sample may also be derived from a subject. Non-limiting examples of samples derived from a subject include plasma, serum, whole blood, urine, semen, milk, tears, saliva, sputum, mucus, spinal fluid, lymph fluid, buccal swabs, vaginal swabs, rectal swabs, aspirates, needle biopsies, or tissue sections of tissue obtained for example by surgery or autopsy. The subject can be a human (e.g., a patient suffering from a disease), a commercially significant mammal, including, for example, a monkey, cow, or horse. Samples can also be obtained from household pets, including, for example, a dog or cat. In some embodiments, the subject is a laboratory animal used as an animal model of disease or for drug screening, for example, a mouse, a rat, a rabbit, or guinea pig.

The labeling compounds disclosed herein are advantageous for differentiation live cells and dead cells. Unlike many other traditional staining agents used for this purpose, for example, the NHS-ester dyes, which requires DMSO as a solvent during preparation, the labeling compounds disclosed herein can be dissolved in an aqueous solution before use. Using an aqueous solution instead of DMSO to dissolve the labeling compounds can avoid many harmful effects associated with DMSO, for example, the penetration of DMSO and the substance dissolved therein into the skin of the user. In addition, the labeling compounds disclosed herein are relatively stable and can be stored in room temperature, for at least 4 days, and thus do not require resuspension just prior to use.

Labelling Intracellular Targets

The methods of the invention may further include a step of labelling intracellular targets in the cells. Such a step typically includes a fixation (or preservation) step that may include contacting the sample with a fixative in an amount sufficient to crosslink proteins, lipids, and nucleic acid molecules. Reagents for fixing cells in a sample are well known to those of skill in the art. Examples include aldehyde-based fixatives, such as formaldehyde, paraformaldehyde, and glutaraldehyde. Other fixatives include ethanol, methanol, osmium tetroxide, potassium dichromate, chromic acid, and potassium permanganate. In some embodiments a fixative may be heating, freezing, desiccation, a cross-linking agent, or an oxidizing agent.

In a typical embodiment, the cells are contacted with a permeabilizing reagent that disrupts or lyses the cytoplasmic membrane, and optionally other membranes, such as the nuclear membrane. The permeabilizing reagent (e.g., detergent) used to permeabilize the cells can be selected based on a variety of factors and can, for example, be an ionic or a non-ionic detergent. Suitable detergents are those that permeabilize cells and retain surface epitope integrity of the proteins being detected. Detergents are typically non-ionic detergents. Exemplary non-ionic detergents include Digitonin and ethyoxylated octylphenol (TRITON X-100®). Other useful permeabilizers (e.g., detergents) include Saponin, Polysorbate 20 (TWEEN® 20), Octylphenoxypoly (ethylene-oxy)ethanol (IGEPAL® CA-630) or Nonidet P-40 (NP-40), Brij-58, and linear alcohol alkoxylates, commercially available as PLURAFAC® A-38 (BASF Corp) or PLURAFAC® A-39 (BASF Corp). In some embodiments, ionic detergents, such as Sodium Dodecyl Sulfate (SDS), Sodium Deoxycholate, or N-Lauroylsarcosine, can be used.

After the cells are fixed and permeabilized they are contacted with a labeled binding agent, which specifically binds to a desired target analyte. Binding agents (e.g., antibodies) useful for these purposes are well known to those of skill in the art. The labelled binding agent can be visualized and/or measured or otherwise identified so that its presence or absence can be detected by means of a detectable signal using means well known to those of skill in the art. Examples include fluorescent molecules, enzymes (e.g., horseradish peroxidase), particles (e.g., magnetic particles), metal tags, chromophores, phosphors, chemiluminescers, specific binding molecules (e.g., biotin and streptavidin, digoxin and antidigoxin), and the like.

The fixing and permeabilizing steps may be used to stain both intracellular and extracellular targets. In some embodiments, staining of both intracellular and extracellular targets is accomplished without the need for centrifugation, for example, using the PerFix-nc®, No Centrifuge Assay kit, available from Beckman-Coulter, Marseille, France. The procedures of using the PerFix-nc®, No Centrifuge Assay kit in intracellular and/or extracellular staining are described in US 2016/0299139, the relevant disclosure of which is incorporated herein by reference.

Measurement Systems

Measurement systems using labelling compounds of the invention to detect live and dead cells in a cell sample are well known. Examples of such systems include flow cytometers, scanning cytometers, imaging cytometers, imaging flow cytometers, fluorescence microscopes, confocal fluorescent microscopes, and mass cytometers.

In some embodiments, flow cytometry may be used to detect fluorescence. A number of devices suitable for this use are available and known to those skilled in the art. Non-limiting examples include Beckman Coulter Navios®, Gallios®, Aquios®, and CytoFLEX® flow cytometers.

Kits

The reagents useful in the methods of the invention can also be produced in the form of kits. Such kits are a packaged combination comprising a container comprising the labelling compounds of the invention in dry form (e.g., as a dried spot on the wall of the container) or in aqueous solution, as well as other reagents, buffers, fixative and permeabilizing solutions, and the like necessary to detect live and dead cells, as well as to stain intracellular targets in the cells. The kits may also comprise instructions on how to perform the method using these reagents.

EXAMPLES

The following examples are offered to illustrate, but not to limit the claimed invention.

Example 1: Staining of Live and Dead Jurkat Cells

The labelling compounds of the invention ViaKrome 405, ViaKrome 561, ViaKrome 638, and ViaKrome 808 (available from Beckman Coulter, Inc. Brea, CA) and used to distinguish live from dead Jukat cells. Briefly, the protocol was as follows:

1. Jurkat cells that had been heated at 55° C. water bath for 10 min were prepared at $5\times10^6$ cells per ml use 100 μl per test ($5\times10^5$ cells per test)
2. Each of the four different labeling compounds, i.e., ViaKrome 405, ViaKrome 561, ViaKrome 638, and ViaKrome 808, were dissolved in 1×PBS and the solutions were added to cell samples at a dose of 2.5 μg labeling compound per test.
3. The mixtures formed after step 2 were vortexed to mix.
4. The samples from step 3 were incubated at 18-25° C. protected from light for 20 min
5. 3 ml of PBS 1× was added to each sample.
6. The samples were then centrifuged for 5 min at 300G
7. The supernatants from the sample were removed by aspiration.
8. 500 μl of PBS 1×/formaldehyde (FA) 0.5% were added to the cells and the samples were analyzed on a CytoFlex flow cytometer.

The results are shown in FIG. 1. The results indicate that dead Jurkat cells showed greater fluorescence than live Jurkat cells when stained with each of the four labeling compounds produced according to Example 1. Compounds that are NHS ester linked to one of the dyes: Violet stain, Red Stain, and Far Red Stain, and obtained from a commercial source, were used as controls to stain the heated Jurkat cells. These NHS ester based compounds are known to preferentially stain dead cells. The results from experiments using these controls were similar to the results from experiments using the labeling compounds of the invention, i.e., dead Jurkat cells showed greater fluorescence than live Jurkat cells.

Example 2: Intracellular and Extracellular Staining of Live and Dead PBMCS

A labeling compound of the invention labeled with ViaKrome 405, ViaKrome 561, ViaKrome 638, or ViaKrome 808 was used to distinguish live from dead peripheral blood mononuclear cells (PBMCs). Briefly, the protocol was as follows:

1. PBMCs that had been heated at 55° C. water bath for 10 min were prepared at $5\times10^6$ cells per ml, 100 μl of which were used per test ($5\times10^5$ cells per test)
2. Labeling compounds as described in Example 1 were dissolved in PBS 1× and the solutions were added to each cell sample at a dose of 2.5 μg labeling compound per test.
3. The mixtures formed from step 2 were vortexed to mix.
4. The samples from step 3 were incubated at 18-25° C. protected from light for 20 min.
5. 3 ml of PBS 1× was added to each sample.
6. The samples were then centrifuged for 5 min at 300G.
7. The supernatants from the sample were removed by aspiration.
8. 500 μl of PBS 1×/formaldehyde (FA) 0.5% were added to resuspend the cells and the samples were analyzed on a CytoFLEX® flow cytometer, Beckman Coulter, Inc.

Figure 2:
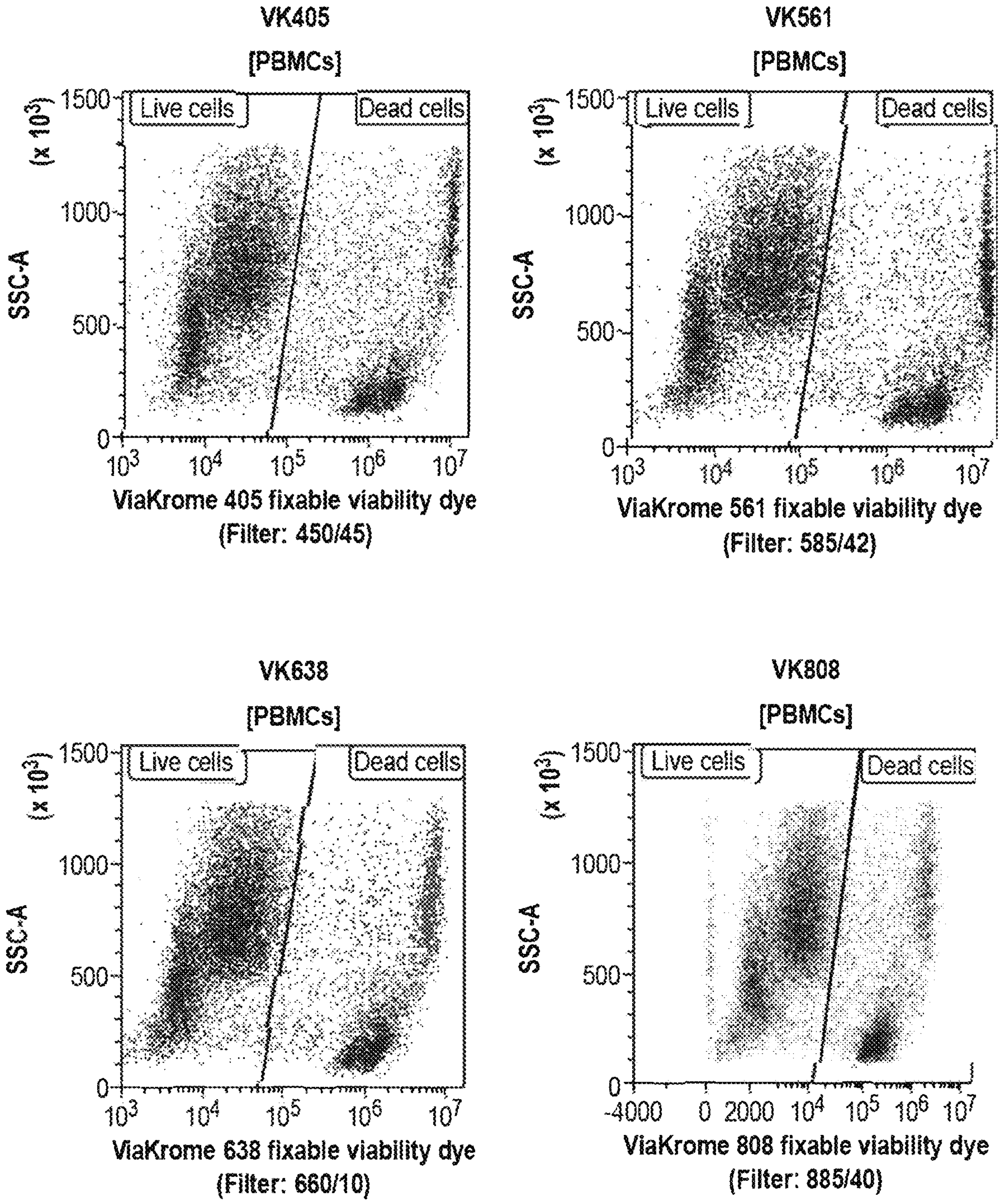
FIG. 2 shows that greater fluoresce from dead peripheral blood mononuclear cells (PBMCs) were detected as compared to live PBMCs, when the PBMCs were stained with labeling compounds of the invention, ViaKrome 405, ViaKrome 561, ViaKrome 638, or ViaKrome 808.

The results are shown in FIG. 2, which indicate that dead PBMCs also showed greater fluorescence signal than live PBMCs.

Example 3: Staining of Live and Dead PBMCS and Intracellular and Extracellular Targets This example shows that the labeling compounds of the invention can be used in combination with staining for intracellular and/or extracellular targets. The labeling compounds were still able to distinguish live versus dead cells even after fixation and permeabilization using PerFix-nc, (Beckman Coulter, Inc). PBMC samples were stained with the labeling compounds followed by a wash to remove unbound labeling compounds. Subsequently cells were fix and permeabilize to stain for intracellular and extracellular antigen with fluorochrome conjugated antibodies according to the protocol as follows:

1. PBMCs that had been heated as described in prepared at $1\times10^7$ cells per ml, 100 μl of which were used per test ($5\times10^5$ cells per test)
2. Labeling compounds as described in Example 2 were dissolved in 1×PBS and the solutions were added to each cell sample at a dose of 2.5 μg labeling compound per test.
3. The mixtures formed after step 2 were vortexed to mix.
4. The samples from step 3 were incubated at 18-25° C. protected from light (for 20 min)
5. 3 ml of 1×PBS was added to each sample.
6. The samples after step 5 were then centrifuged for 5 min at 300G.
7. 50 μl of 100% fetal calf serum (FCS) were added to each sample.

8. 2.5 μl of PerFix-nc reagent 1 (Fixative solution) were added to each sample to mix.
9. The mixtures from step 8 were incubated for 15 min at 18-25° C., protected from light
10. 150 μl PerFix-nc reagent 2 (Permeabilizing solution) and antibody conjugates (10 μl Granzyme B-FITC (PN B46038, Beckman Coulter), 10 μl CD19-PE (PN A07769, Beckman Coulter), 5 μl CD14-ECD (PN B92391, Beckman Coulter), 5 μl CD79a-PC5.5 (PN B42018, Beckman Coulter), 5 μl CD3-PC7 (PN737657, Beckman Coulter), and 5 μl CD45-KrO (PN A96416, Beckman Coulter) were added to the samples and mix.
11. The mixture formed by step 10 was incubated for 15 min at 18° C.-25° C., protected from light
12. 3 ml of PerFix-nc reagent 3 (10×) diluted to 1× (in water) and added to the mixture above.
13. The mixture was then centrifuged for 5 min at 500G.
14. The supernatant from each sample was removed by aspiration.
15. 500 μl of PBS 1×/formaldehyde (FA) 0.5% were added to the cells and the samples were analyzed on a CytoFlex® flow cytometer.

Figure 3A:
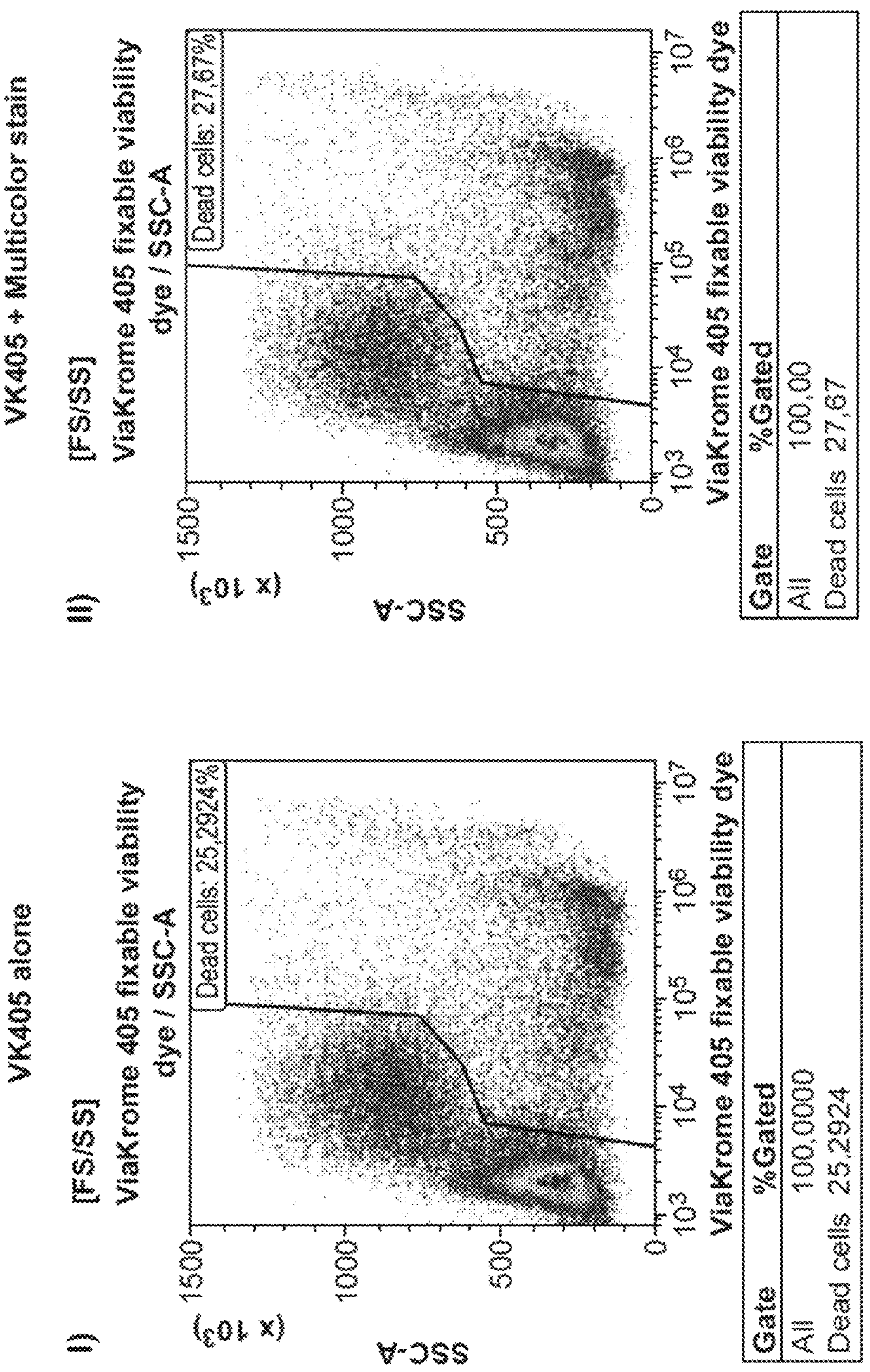
FIG. 3A-3B show a representative data set demonstrating that the labeling compounds of invention were able to differentiate live cells from dead cells, even when used in combination with intracellular antigen staining. Specifically.
Figure 3B:
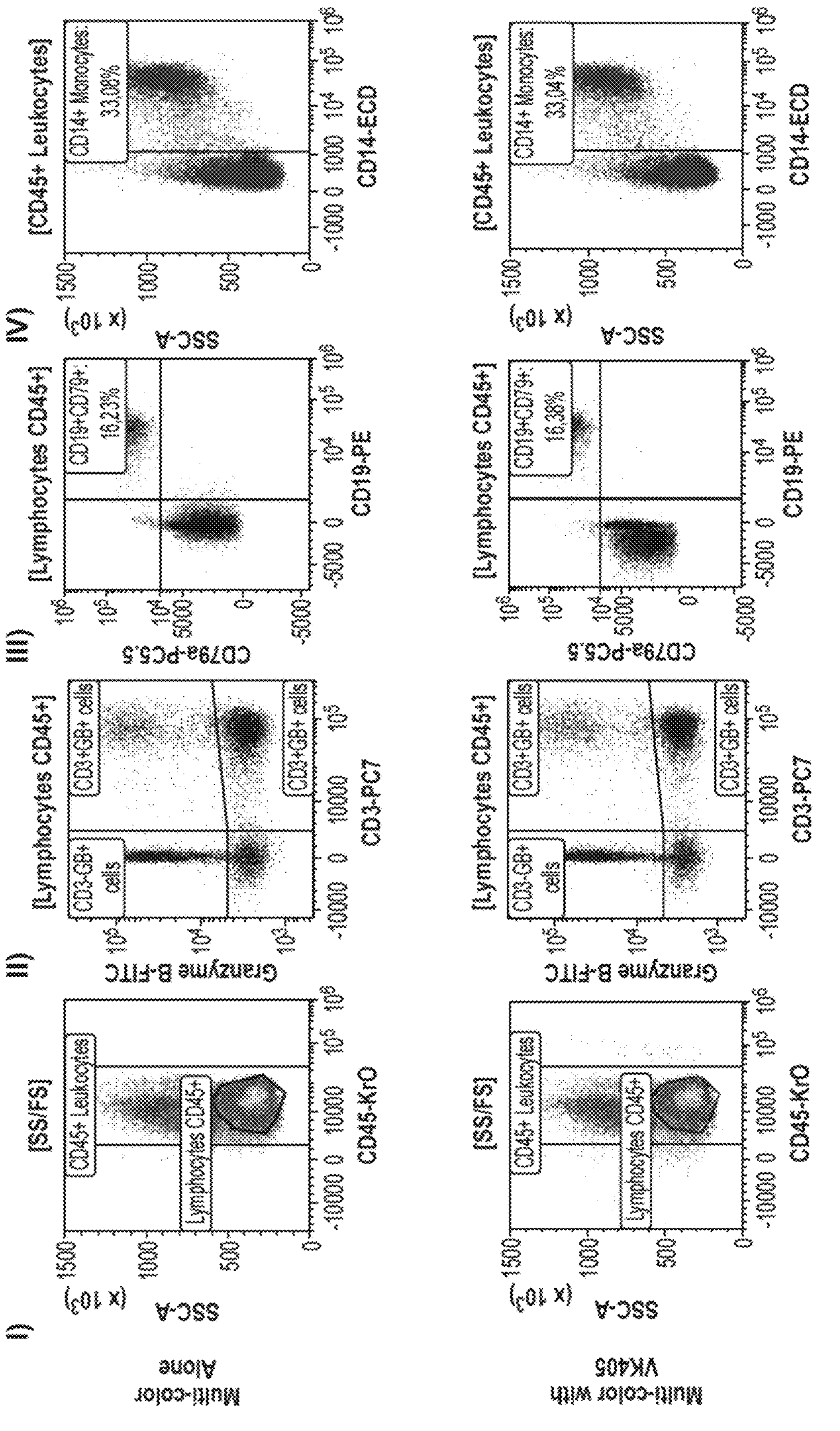

The results are shown in FIGS. 3A and 3B. FIG. 3A the left panel shows the results of cells that have been stained with the labeling compound of the invention, ViaKrome 405. FIG. 3A right panels shown the staining of anti-CD45, anti-CD3, anti-CD19, and anti CD14, respectively. In FIG. 3B, the cells were stained with labeling compound prior to staining with one of the conjugates. The results show that the labeling compounds of the invention allows detection of dead cells even after processing the samples using buffers for intracellular staining and that the percentage of dead cells was similar when the labeling compounds of the invention were used alone or when used in combination with an antibody conjugate. In addition, the percentages of cells that express specific targets (e.g., CD45) were also similar between cell samples stained with antibody conjugates alone and cell samples stained with the antibody conjugates and the ViaKrome 405. Hence, staining procedures using the labeling compounds of invention does not change the possibility to detect specific antigen (intracellular and extracellular) by specific antibody/Fluorochrome conjugates.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for distinguishing dead cells from live cells in a cell sample, the method comprising:

contacting the cell sample with a labelling compound of formula:

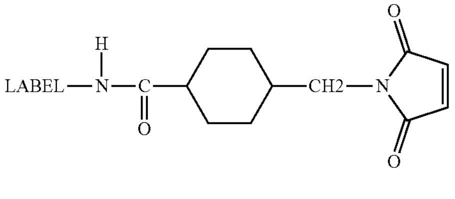

wherein LABEL is a fluorescent label, wherein the labelling compound has a molecular weight of 714.69 g/mol and an excitation/emission wavelength of 402 nm/425 nm, a molecular weight of 1186.27 g/mol and an excitation/emission wavelength of 638 nm/652 nm, or a molecular weight of 1647.66 g/mol and an excitation/emission wavelength of 852 nm/877 nm, under conditions whereby the labelling compound binds free thiol groups on cell surface proteins on dead cells and live cells and preferentially crosses cell membranes of dead cells and binds free thiol groups on intracellular proteins in the dead cells; and detecting the label in the cell sample, thereby distinguishing dead cells from live cells in the cell sample by detecting increased labelling of the dead cells, as compared to live cells, and as compared to a control cell sample stained with an NHS ester compound based dye.

2. The method of claim 1, wherein the method further comprises labelling intracellular targets in the cells after the step of contacting the cell sample with the labelling compound.

3. The method of claim 2, wherein the step of labelling intracellular targets includes fixing and permeabilizing the cells.

4. The method of claim 2, wherein the method further comprises labelling extracellular targets.

5. The method of claim 1, wherein the conditions include a pH of between 6.5 and 7.5.

6. The method of claim 1, wherein the labeling of dead cells is at least 20 times the labeling of live cells.

7. The method of claim 1, wherein the step of contacting includes incubating the cell sample with the labelling compound for between 10 and 60 minutes.

8. The method of claim 1, wherein the step of detecting the label in the cell sample is carried out using a flow cytometer.

9. The method of claim 1, wherein the cell sample is a blood cell sample.

10. The method of claim 1, wherein the cell sample is from a human.

* * * * *